(12) United States Patent
Herrin

(10) Patent No.: US 12,569,646 B2
(45) Date of Patent: Mar. 10, 2026

(54) SYSTEMS AND METHODS FOR PERFORMING TISSUE BIOPSY

(71) Applicant: Olympus Medical Systems Corporation, Hachioji (JP)

(72) Inventor: David A. Herrin, Seattle, WA (US)

(73) Assignee: Olympus Medical Systems Corporation, Tokyo (JP)

( * ) Notice: Subject to any disclaimer, the term of this patent is extended or adjusted under 35 U.S.C. 154(b) by 976 days.

(21) Appl. No.: 17/574,120

(22) Filed: Jan. 12, 2022

(65) Prior Publication Data

US 2022/0218945 A1 Jul. 14, 2022

Related U.S. Application Data

(60) Provisional application No. 63/136,226, filed on Jan. 12, 2021.

(51) Int. Cl.
| | |
|---|---|
| *A61M 25/00* | (2006.01) |
| *A61B 10/02* | (2006.01) |
| *A61B 10/04* | (2006.01) |
| *A61M 25/10* | (2013.01) |

(52) U.S. Cl.
CPC ..... *A61M 25/0026* (2013.01); *A61B 10/0283* (2013.01); *A61M 25/10185* (2013.11); *A61B 2010/045* (2013.01)

(58) Field of Classification Search
CPC ................ A61B 10/0283; A61B 10/04; A61B 2010/045; A61M 25/0026; A61M 25/10185
See application file for complete search history.

(56) References Cited

U.S. PATENT DOCUMENTS

| | | | | | |
|---|---|---|---|---|---|
| 4,532,935 | A | * | 8/1985 | Wang ................ | A61B 10/0283 600/566 |
| 5,261,889 | A | * | 11/1993 | Laine .................... | A61M 37/00 604/164.11 |
| 2011/0087173 | A1 | * | 4/2011 | Sibbitt, Jr. ......... | A61B 10/0233 604/207 |
| 2011/0224642 | A1 | * | 9/2011 | Fojtik .................... | A61M 1/67 604/207 |
| 2012/0323142 | A1 | * | 12/2012 | Allen ............... | A61B 5/150572 600/576 |
| 2013/0261559 | A1 | * | 10/2013 | Werbickas .......... | A61M 5/3257 604/198 |
| 2017/0021144 | A1 | * | 1/2017 | Kanner ........... | A61M 25/10185 |

* cited by examiner

*Primary Examiner* — Alex M Valvis
*Assistant Examiner* — Anna Roberts
(74) *Attorney, Agent, or Firm* — Schwegman Lundberg & Woessner, P.A.

(57) ABSTRACT

Various disclosed embodiments include illustrative apparatuses, systems, and methods for providing a vacuum force during tissue biopsies. In an illustrative embodiment, an illustrative apparatus includes a housing that is attachable to a handle of a medical device and a piston device that is disposed at least partially within the housing. The piston device is configured to be biased in a first direction and lockable in a loaded pre-suction position.

13 Claims, 6 Drawing Sheets

SYSTEMS AND METHODS FOR PERFORMING TISSUE BIOPSY

BACKGROUND

The statements in this section merely provide background information related to the present disclosure and may not constitute prior art.

In current biopsy procedures, such as in fine needle aspiration (FNA) biopsy, a vacuum syringe is used to provide a suction force to assist a needle to aspirate tissue. As shown in FIG. 1, a syringe, such as that produced by Vaclok™ is attached to a stopcock. The stopcock is then attached to an aspirating handle portion of a needle handle that is attached to a working channel port of an endoscope. This procedure requires multiple steps including opening the stopcock and drawing vacuum by pulling the piston of the syringe proximally. As such, this procedure requires help from an additional operator because attaching the stopcock and the syringe as well as operating there syringe require two hands to operate.

BRIEF SUMMARY

Various disclosed embodiments include illustrative apparatuses, systems, and methods for providing a vacuum force during tissue biopsies.

In an illustrative embodiment, an illustrative apparatus includes a housing that is attachable to a handle of a medical device and a piston device that is disposed at least partially within the housing. The piston device is configured to be biased in a first direction and lockable in a loaded pre-suction position.

In another illustrative embodiment, an illustrative system includes a medical device and an apparatus. The medical device includes a handle and an insertion portion. The apparatus includes a housing that is attachable to a handle of a medical device and a piston device that is disposed at least partially within the housing. The piston device is configured to be biased in a first direction and walkable in a loaded pre-suction position.

In another illustrative embodiment, an illustrative method includes moving a piston device disposed at least partially within a housing into a lockable pre-suction position, attaching a distal end of the housing to an aspiration device, and releasing the piston device from the lockable pre-suction position.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

Illustrative embodiments are illustrated in referenced figures of the drawings. It is intended that the embodiments and figures disclosed herein are to be considered illustrative rather than restrictive.

Like reference symbols in the various drawings generally indicate like elements.

DETAILED DESCRIPTION

Figure 1:
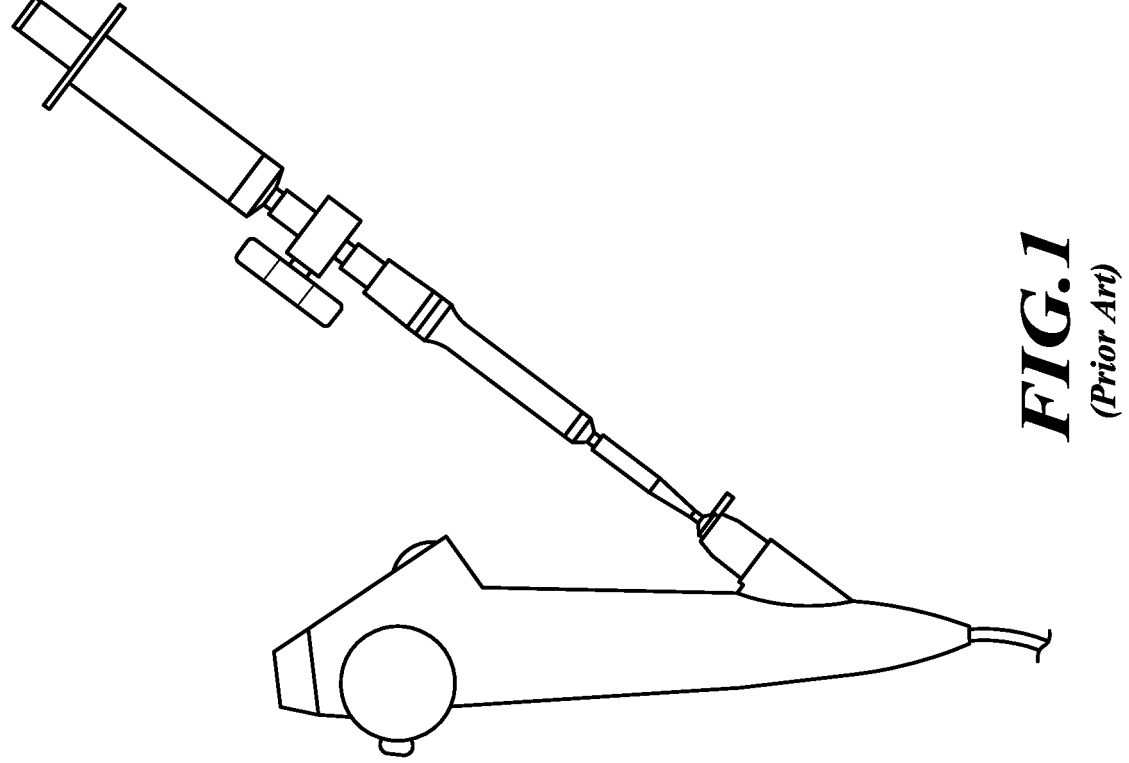
FIG. 1 is a side plan view of an exemplary prior art system.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Various disclosed embodiments include illustrative apparatuses, systems, and methods for producing continuous or near continuous vacuum while aspirating tissue.

Figure 2:
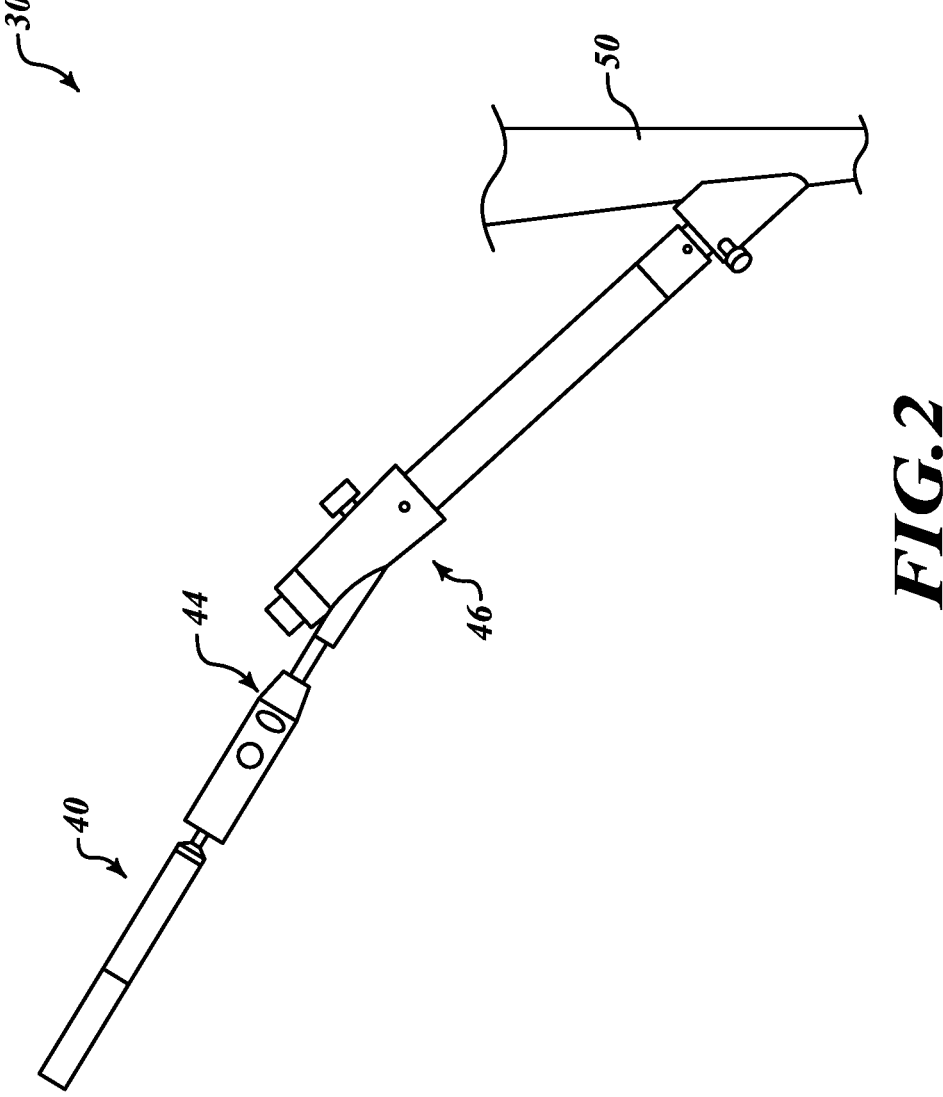
FIG. 2 is a side plan view of an illustrative tissue biopsy system.

Referring now to FIG. 2 and given by way of overview, in various embodiments an illustrative system 30 includes a scope 50 (partial scope shown), a multi-lumen catheter system 46 (handle portion shown), an aspirating device 44 (handle portion shown), and a vacuum-creating device 40.

It will be appreciated that, in various embodiments, the scope 50 may be any of a number of different types of scopes used in medical procedures. The scope 50 may include multi-use or single-use endoscopes, such as bronchoscopes, laparoscope, laryngoscope, etc. The multi-lumen catheter system 46 may be any device that includes two or more lumens located within an insertion tube attached to a handle device with ports for accessing the lumens. The lumens of the multi-lumen catheter system 46 may be suitable for receiving imaging devices (not shown) and various types of medical devices, such as the aspirating device 44. The received imaging devices may include cameras or ultrasound devices, such as a radial ultrasound probe or comparable devices. In various embodiments, the multi-lumen catheter system 46 may include a base section rotatably coupled to the scope 50 and a port section slidably received by the base section. An exemplary multi-lumen catheter system 46 is shown and described in U.S. Provisional Patent Application No. 63/123,731, filed Dec. 10, 2020, the contents of which are hereby incorporated by reference.

In various embodiments, the insertion tube of the multi-lumen catheter system 46 is received within a working channel port of the scope 50. The multi-lumen catheter system 46 may be attached to the working channel port. The medical device 44 may include a flexible sheath attached to a first portion of a handle and a flexible operational tool received within the flexible sheath and attached to an actuator portion of the handle. The operational tool may include a tissue aspiration device, such as a flexible needle, a cytology brush or comparable devices. The operational tool may include a lumen that is in communication with a corresponding lumen within the first portion and the actuator portion of the handle.

In various embodiments, the vacuum-creating device 40 sealably attaches to the handle of the aspirating device 44, such that the vacuum-creating device 40 maintains sealed communication with the lumens of the operational tool and the first portion and the actuator portion of the handle of the aspirating device 44.

Figure 3:
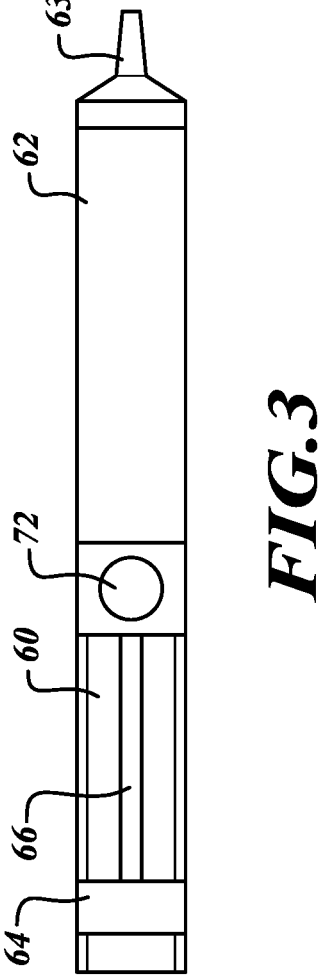
FIG. 3 is a side plan view in partial cutaway of an illustrative vacuum device.
Figure 4:
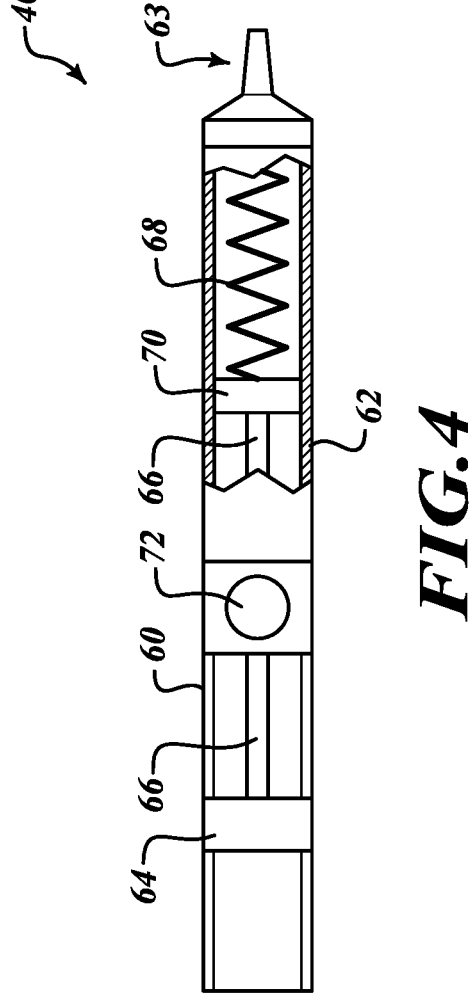
FIG. 4 is a side plan view in partial cut-away of the vacuum device of FIG. 3.

Referring additionally to FIGS. 3 and 4, in various embodiments the vacuum-creating device 40 is a straight-line pump capable of repeatedly drawing a vacuum. The vacuum-creating device 40 includes a pump chamber 62, an attachment device 63, a piston 70 slidably received within the pump chamber 62, a piston rod 66, a thumb rest 64, a biasing device 68, and a release button 72. The piston rod 66 attaches to the piston 70 within the pump chamber 62. The thumb rest 64 connects at or near a proximal end of the piston rod 66.

In various embodiments, the attachment device 63 may be a Luer fitting or other fitting depending upon the device that the vacuum-creating device 40 will attach thereto.

The vacuum-creating device 40 may include a proximal housing portion 60. The proximal housing portion 60 is a partially exposed track for slidably receiving the thumb rest 64. In various embodiments, the proximal housing portion 60 has a C-shaped cross-section or other configurations depending upon the shape of the received thumb rest 64.

In various embodiments, the biasing device 68 may be any type of device, such as a spring, that, when compressed by the piston 70 distally within the pump chamber 62, exerts a proximal force on the piston 70.

In various embodiments, the thumb rest 64 or the proximal end of the piston rod 66 (in absence of the thumb rest 64) includes a first feature (not shown) capable of attaching to a second feature (not shown) of the release button 72. The second feature is located within the vacuum-creating device 40. The release button 72 may be biased such that the second feature is engaged with the first feature when the first and second features are co-located longitudinally and no external forces are applied to the release button 72. Once a user applies a force above a threshold to the release button 72, the second feature disengages from the first feature allowing the biasing device 68 to force the piston 70 and the piston rod 66 proximally within the vacuum-creating device 40. The motion of the piston 70 proximally results in creation of lower air pressure at the distal side of the piston 70 within the pump chamber 62. The lower air pressure is experienced at whatever device is connected to the attachment device 63. If the aspirating device 44 is attached to the attachment device 63, then the lower air pressure causes a drawing action at the distal end of the aspirating device 44 for aiding in the sampling of tissue, fluid or other target material. The first and/or second features may include a ramp and a flange (not shown) to allow for engagement when the thumb rest 64 is moved distally to a pre-suction position.

Figure 6:
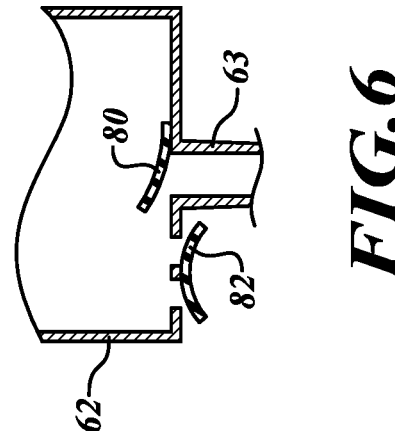
FIG. 6 is a partial cross-sectional view of the vacuum device of FIG. 3.
Figure 5:
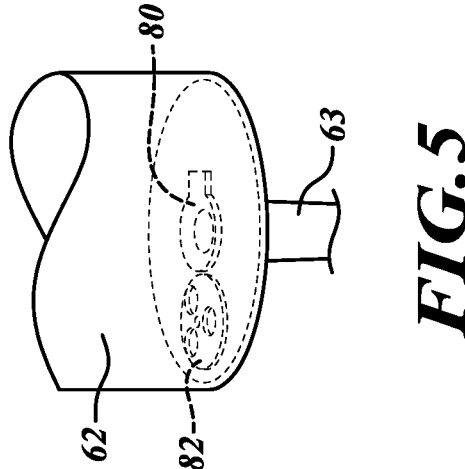
FIG. 5 is a partial hidden-line perspective view of the vacuum device of FIG. 3.

Referring additionally to FIGS. 5 and 6, in various embodiments a base or distal section of the pump chamber 62 includes an intake valve 80 and an exhaust valve 82. The intake valve 80 maintains a closed position between the pump chamber 62 and a lumen within the attachment device 63 when air pressure within the attachment device 63 or whatever is connected to the attachment device 63 is equal to or less than air pressure within the pump chamber 62. The intake valve 80 is in an opened position when the air pressure within the attachment device 63 or whatever is connected to the attachment device 63 is greater than the air pressure within the pump chamber 62.

The exhaust valve 82 is located between a wall of the pump chamber 62 and an exterior environment of the pump chamber 62. The exhaust valve 82 is in an opened position when the air pressure within the pump chamber 62 is greater than air pressure of the exterior environment of the pump chamber 62. The exhaust valve 82 is in a closed position when the air pressure within the pump chamber 62 is less than the air pressure of the exterior environment of the pump chamber 62. Examples of the intake valve 80 and the exhaust valve 82 include but are not limited to flapper valves, umbrella valves, duckbill valves, or comparable one-way valves.

Figure 7:
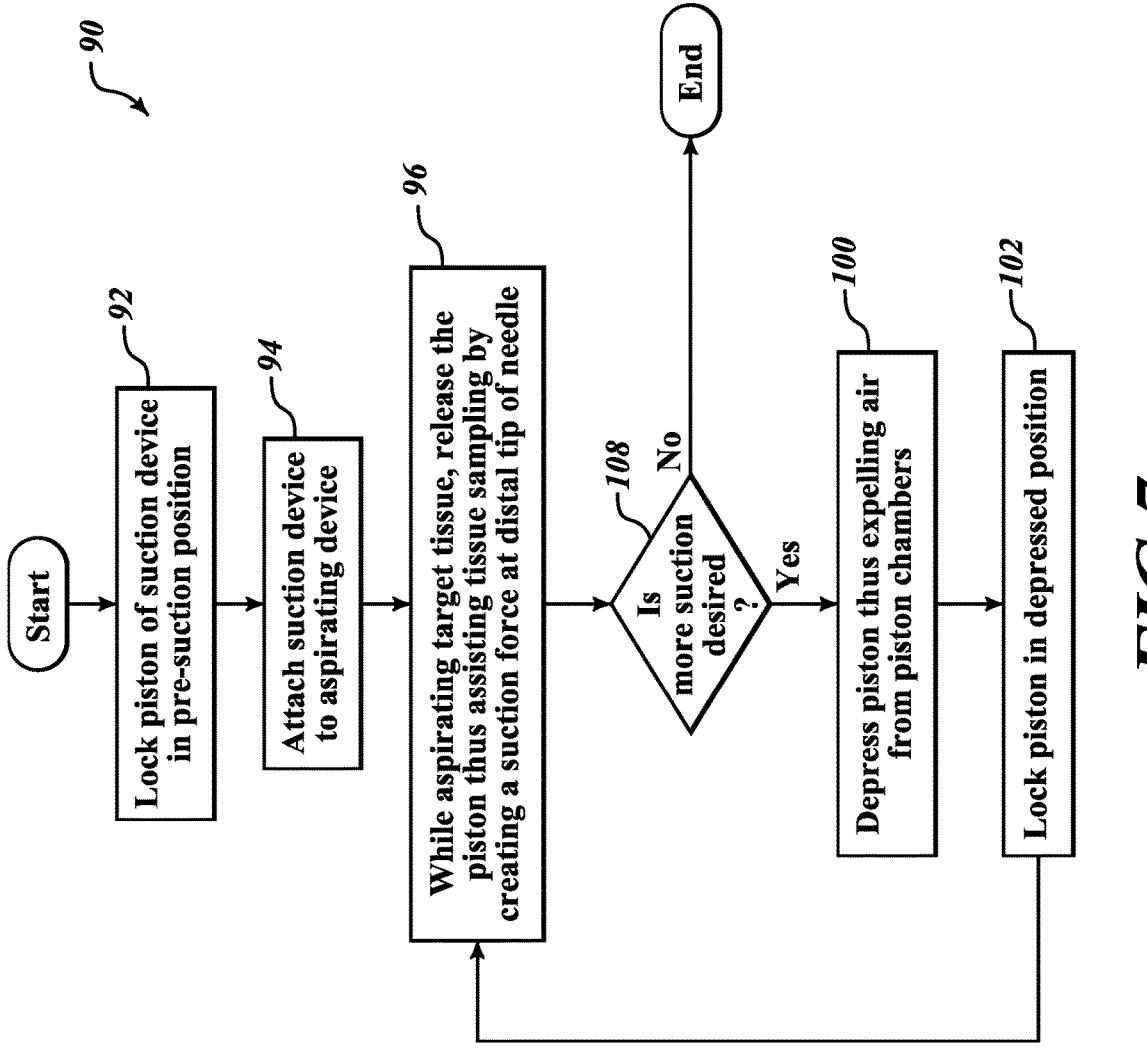
FIG. 7 is a flowchart of a method performed by an illustrative tissue biopsy system.

Referring additionally to FIG. 7, in various embodiments an illustrative method 90 is provided for enabling tissue biopsies. At a block 92, an operator locks the piston 70 of the vacuum-creating (suction) device 40 in a pre-suction position. At a block 94, the operator attaches the vacuum-creating device 40 to the aspirating device 44. It will be appreciated that, in various embodiments, the block 92 may be performed after that of block 94. At a block 96, while the operator is either activating the aspirating device 44 in order to actively aspirate target tissue or just has a sampling portion of the aspirating device 44 currently engaged with target tissue, the vacuum-creating device 40 is activated. The activated vacuum-creating device 40 produces a proximal suction force at a distal end of the vacuum-creating device 40 and within the aspirating device 44. This action is performed by depressing the release button 72 of the vacuum-creating device 40.

At a decision block 98, if the operator determines that no more suction is desired, then the process 90 ends, whereby the aspirating device 44 and anything attached to it are removed from the patient and the tissue received within the tissue aspirating device is removed for analysis. If the operator determines at the decision block 98 that more suction is desired in order to improve the tissue sampling, then at a block 100 the operator depresses the piston 70, thus expelling air from piston chamber 62. At a block 102, when the operator depresses the piston 70 far enough, the piston 70 is locked at the pre-suction position, whereby the process 90 returns to the block 96.

From the foregoing discussion and associated drawing figures, it will be appreciated that various embodiments have been disclosed and illustrated. To that end and without any implication of any limitation (which is not to be inferred), the following paragraphs set forth non-limiting summaries of various embodiments disclosed herein by way of example only and not of limitation:

A. An apparatus comprising: a housing attachable to a handle of a medical device; and a piston device disposed at least partially within the housing, the piston device being configured to be biased in a first direction and lockable in a loaded pre-suction position.

B. The apparatus of A, further comprising a fitting disposable at the distal end of the housing and configured to be attached to a handle of a medical device, wherein: the housing further includes a piston housing having a proximal end and a distal end; and the piston device further includes: a piston slidably receivable within the piston housing, the piston being configured to create a seal between the proximal end and the distal end of the piston housing; a piston rod having: a distal end couplable to the piston; and a proximal end located external to the piston housing; a biasing device disposed within the piston housing between the piston and the distal end of the piston housing; and a latch being configured to maintain the piston rod in a cocked position, the piston being configured to compress the biasing device responsive to the piston rod being in the cocked position.

C. The apparatus of B, wherein the fitting includes a Luer fitting.

D. The apparatus of B, wherein the biasing device includes a spring.

E. The apparatus of B, further comprising an intake valve disposed between the piston housing and the fitting, the intake valve being configured to allow air to flow proximately into the piston housing.

F. The apparatus of E, further comprising an exhaust valve disposed at the distal end of the piston housing, the exhaust valve being configured to allow air to flow from within the piston housing to an exterior of the piston housing.

G. A system comprising: a medical device including: a handle; and an insertion portion; and an apparatus including: a housing attachable to a handle of a medical device; and a piston device disposed at least partially within the housing, the piston device being configured to be biased in a first direction and walkable in a loaded pre-suction position.

H. The system of G, wherein: the apparatus further includes a fitting disposable at the distal end of the housing and configured to be attached to the handle of the medical device; the housing further includes a piston housing having a proximal end and a distal end; and the piston device further includes: a piston slidably receivable within the piston housing, the piston being configured to create a seal between the proximal end and the distal end of the piston housing; a piston rod having: a distal end couplable to the piston; and a proximal end located external to the piston housing; a biasing device disposed within the piston housing between the piston and the distal end of the piston housing; and a latch being configured to maintain the piston rod in a cocked position, the piston being configured to compress the biasing device when the piston rod is in the cocked position.

I. The system of H, wherein the apparatus further includes an intake valve disposed between the piston housing and the fitting, the intake valve being configured to allow air to flow proximately into the piston housing.

J. The system of I, wherein: the apparatus further includes an exhaust valve disposed at the distal end of the piston housing; and the exhaust valve is configured to allow air to flow from within the piston housing to an exterior of the piston housing.

K. The system of H, wherein: the medical device includes a needle; and the handle includes a stylet inlet port couplable to the fitting.

L. The system of K, wherein the fitting and the stylet inlet port comprise Luer fittings.

M. The system of H, wherein the medical device includes: a multi-lumen catheter device, wherein: the insertion portion includes a flexible insertion tube including two or more lumen; the handle is configured to couple to an endoscope, the handle including: a base section; and an inlet port being configured to be slidably received longitudinally relatively to the base section; and a needle device including a handle with a stylet inlet port couplable to the fitting.

N. The system of M, wherein the fitting and the stylet inlet port include Luer fittings.

O. The system of H, wherein the biasing device includes a spring.

P. A method comprising: moving a piston device disposed at least partially within a housing into a lockable pre-suction position; attaching a distal end of the housing to an aspiration device; and releasing the piston device from the lockable pre-suction position.

Q. The method of P, further comprising: applying a proximal biasing force to a piston of the piston device responsive to the moving of the piston device.

R. The method of P, wherein: the moving includes latching the piston device to the housing; and the releasing includes delatching the piston device from the housing.

S. The method of Q, further comprising: expelling air from the housing through a first one-way valve and blocking air from entering the housing via a second one-way valve responsive to the releasing of the piston device.

T. The method of S, further comprising: receiving air into the housing via the second one-way valve, thereby blocking air from exiting the first one-way valve responsive to the piston device moving in a proximal direction within the housing.

In some instances, one or more components may be referred to herein as "configured to," "configured by," "configurable to," "operable/operative to," "adapted/adaptable," "able to," "conformable/conformed to," etc. Those skilled in the art will recognize that such terms (for example "configured to") generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (for example, "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (for example, the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While the disclosed subject matter has been described in terms of illustrative embodiments, it will be understood by those skilled in the art that various modifications can be made thereto without departing from the scope of the claimed subject matter as set forth in the claims.

What is claimed is:

1. A system comprising:
   a medical device including:
      a handle; and
      an insertion portion; and
   a vacuum-creating apparatus configured to repeatably generate vacuum, the vacuum-creating apparatus including:
      a housing attachable to the handle of the medical device to deliver a vacuum force generated by the vacuum-creating apparatus to the medical device;
      a piston device disposed at least partially within the housing, the piston device being configured to; be biased in a first direction, operate between a pre-suction position and a released position, generate the vacuum force within the housing upon release from the pre-suction position, repeatably operate between the pre-suction position and the released position to generate the vacuum force, and be lockable in the pre-suction position;
      a latch engageable with the piston device to lock the piston device in the pre-suction position;
      a release button configured to disengage the latch and release the piston device from the pre-suction position;
      an intake valve disposed between the housing and the medical device, the intake valve configured to allow air to flow into the housing during operation; and
      an exhaust valve disposed at a distal end of the housing, the exhaust valve configured to allow air to flow out of the housing during operation.

2. The system of claim 1, wherein:
   the vacuum-creating apparatus further includes a fitting disposable at the distal end of the housing and configured to be attached to the handle of the medical device;

the housing further includes a piston housing having a proximal end and a distal end; and
the piston device further includes:
a piston slidably receivable within the piston housing, and the piston is configured to create a seal between the proximal end and the distal end of the piston housing;
a piston rod having:
   a distal end couplable to the piston; and
   a proximal end located external to the piston housing; and
a biasing device disposed within the piston housing between the piston and the distal end of the piston housing, wherein
the latch being configured to maintain the piston rod in a cocked position, the piston being configured to compress the biasing device when the piston rod is in the cocked position.

3. The system of claim 2, wherein:
   the medical device includes a needle; and
   the handle includes a stylet inlet port couplable to the fitting.

4. The system of claim 3, wherein the fitting and the stylet inlet port comprise Luer fittings.

5. The system of claim 2, wherein the medical device includes:
   a multi-lumen catheter device, wherein:
   the insertion portion includes a flexible insertion tube including two or more lumen;
   the handle is configured to couple to an endoscope, the handle including:
   a base section; and
   an inlet port being configured to be slidably received longitudinally relatively to the base section; and
   a needle device including a handle with a stylet inlet port couplable to the fitting.

6. The system of claim 5, wherein the fitting and the stylet inlet port include Luer fittings.

7. The system of claim 2, wherein the biasing device includes a spring.

8. An apparatus comprising:
   a housing attachable to a handle of a medical device to deliver a vacuum force generated by the apparatus to the medical device, wherein the medical device includes an insertion portion; and
   a piston device disposed at least partially within the housing, the piston device being configured to: be biased in a first direction, operate between a pre-suction position and a released position, generate the vacuum force within the housing upon release from the pre-suction position, repeatably operate between the pre-suction position and the released position to generate the vacuum force, and be lockable in a loaded pre-suction position, wherein:
   the housing further includes a piston housing having a proximal end and a distal end; and
   the piston device further includes:
   a piston slidably receivable within the piston housing, the piston being configured to create a seal between the proximal end and the distal end of the piston housing, the seal enabling the piston to repeatably generate a vacuum force within the piston housing between the distal end of the piston housing and the piston upon movement of the piston in a proximal direction;
   a piston rod having:
   a distal end couplable to the piston; and
   a proximal end located external to the piston housing;

a biasing device disposed within the piston housing between the piston and the distal end of the piston housing;

a latch being configured to maintain the piston rod in a cocked position, the piston being configured to compress the biasing device responsive to the piston rod being in the cocked position; and a release button configured to disengage the latch and release the piston from the pre-suction position to generate vacuum within the housing;

an intake valve disposed between the piston housing and an exit fitting, the intake valve being configured to allow air to flow proximately into the piston housing; and an exhaust valve disposed at the distal end of the piston housing, the exhaust valve being configured to allow air to flow from within the piston housing to an exterior of the piston housing.

9. The apparatus of claim 8, wherein the housing includes a fitting and the fitting includes a Luer fitting.

10. The apparatus of claim 8, wherein the biasing device includes a spring.

11. The apparatus of claim 8, wherein: the intake valve is configured to maintain a closed position when air pressure within the exit fitting is equal to or less than air pressure within the piston housing; and the exhaust valve is configured to maintain a closed position when air pressure within the piston housing is less than exterior air pressure.

12. The apparatus of claim 8, wherein:

the release button includes a first engagement feature;

the piston rod includes a second engagement feature;

the first and second engagement features are configured to engage when the piston is moved to the pre-suction position; and the engagement is maintained until a threshold release force is applied to the release button.

13. The apparatus of claim 8, wherein:

the intake valve and the exhaust valve each comprise a valve type selected from a group consisting of:

a flapper valve, an umbrella valve, and a duckbill valve;

wherein the valve type is selected to provide specific pressure thresholds for controlling air flow into and out of the piston housing.

* * * * *